United States Patent [19]

Emling et al.

[11] Patent Number: 5,504,189
[45] Date of Patent: Apr. 2, 1996

[54] PEPTIDES, THEIR PREPARATION AND USE

[75] Inventors: Franz Emling, Ludwigshafen; Andreas Haupt, Oberursel; Michael Kluge, Kallstadt; Matthias Kroner, Eisenberg-Steinborn; Gerhard Haas, Wehr; Ulrich Schmidt, Stuttgart; Helmut Griesser, Gerlingen; Bernd Riedl, Stuttgart, all of Germany

[73] Assignee: BASF Aktiengesellschaft, Ludwigshafen, Germany

[21] Appl. No.: 162,182

[22] PCT Filed: Jun. 17, 1992

[86] PCT No.: PCT/EP92/01304

§ 371 Date: Dec. 16, 1993

§ 102(e) Date: Dec. 16, 1993

[87] PCT Pub. No.: WO93/00362

PCT Pub. Date: Jan. 7, 1993

[30] Foreign Application Priority Data

Jun. 20, 1991 [DE] Germany .......................... 41 20 327.5

[51] Int. Cl.$^6$ .............................. C07K 5/00; C07K 7/00; C07K 17/00; A61K 38/00
[52] U.S. Cl. ............................................................ 530/317
[58] Field of Search ........................ 514/9, 11; 530/317

[56] References Cited

U.S. PATENT DOCUMENTS

| 4,493,796 | 1/1985 | Rinehart, Jr. . | |
|---|---|---|---|
| 4,548,814 | 10/1985 | Rinehart, Jr. | 424/95 |
| 4,782,135 | 11/1988 | Rinehart, Jr. | 530/317 |
| 4,948,791 | 8/1990 | Rinehart, Jr. et al. | 514/183 |

OTHER PUBLICATIONS

Morrison and Boyd, Organic Chemistry, 3rd edition, p. 186, (1980).
ASM News vol. 56 p. 368 (1990).
Sandstrom et al. Drugs vol. 43 pp. 372–390 (1987).
Jaroff, Time May 23, 1988, pp. 56–64.
Johnson et al. Cancer Treatment Reviews vol. 2 pp. 1–31 (1975).
25th Ann. vol., Annual Reports In Medicinal Chemistry vol. 25, 1992 Total Synthesis of the Didemnins; . . . Synthesis, Schmidt et al., 294–300.
Anrineoplastic Activity of Didemnin Congeners: . . . , Jourin et al., Jr. of Med. Chem 1991, vol. 34, No. 2, 486–491.

*Primary Examiner*—Howard E. Schain
*Assistant Examiner*—Sheela J. Huff
*Attorney, Agent, or Firm*—Keil & Weinkauf

[57] ABSTRACT

Antitumor peptides of the formula

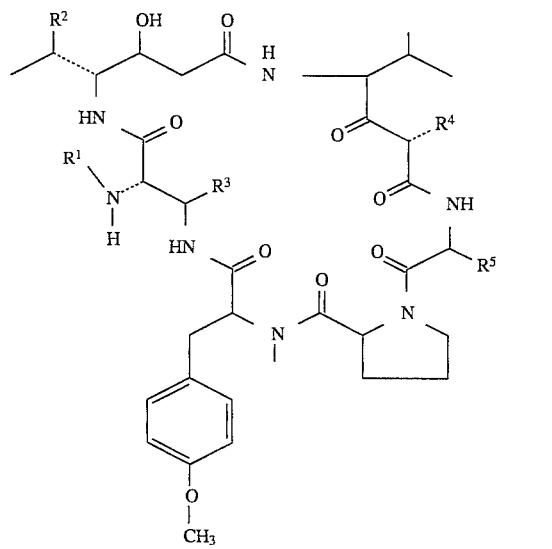

where $R^1$, $R^2$, $R^3$, $R^4$ and $R^5$ have the meanings stated in the description, and the preparation thereof.

1 Claim, No Drawings

PEPTIDES, THEIR PREPARATION AND USE

The present invention relates to novel peptides, to their preparation and to their use in controlling diseases.

Various compounds have been isolated from tunicates of the species Trididemnum solidum and Trididemnum cyanophorum, and their structure has been elucidated (U.S. Pat. Nos. 4,493,796, 4,548,814, 4,782,135, EP 48 149, EP 393 883) and they have been found to have antiviral and antineoplastic effects.

We have now found that peptides of the formula I

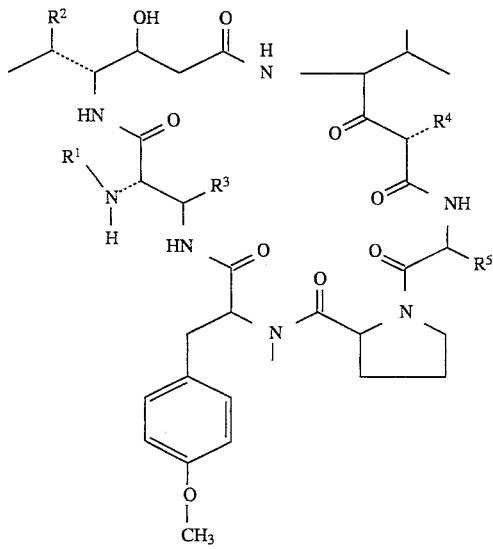

where
$X^1$ is oxygen or NH,
$X^2$ is oxygen or NH,
$R^1$ is an amino-protective group, a linear, branched or alicyclic saturated or unsaturated aliphatic, aliphatic-aromatic or aromatic acyl radical which has 1–30 carbons and can be substituted by fluorine, nitro, oxo, hydroxyl, $C_1$–$C_4$-alkoxy or unprotected or protected amino,
$R^2$ is hydrogen, methyl or ethyl,
$R^3$ is hydrogen or methyl,
$R^4$ is hydrogen or methyl,
$R^5$ is hydrogen or $C_1$–$C_4$-alkyl and
$R^6$ is hydrogen or methyl, except the compounds in which $X^1$ and $X^2$ are both oxygen,
$R^3$ and $R^4$ are both methyl, $R^5$ is isopropyl and $R^1$ is protected or free N—Me—D—Leu, and the salts thereof with physiologically tolerated acids, are easier to prepare and have an improved effect.

The N,O-dimethyltyrosyl radical can have the R or S configuration in the molecule.

Preferred compounds of the formula I are those where
$X^1$ is NH,
$X^2$ is NH,
$R^1$ is H, aliphatic $C_1$–$C_{10}$-acyl, a urethane amino-protective group, a benzoyl radical which is unsubstituted or substituted by Cl or OH, a D-aminoacyl group which is free or N-terminally protected, or the sarcosyl radical,
$R^2$ is $CH_3$ or $C_2H_5$,
$R^3$ is hydrogen or methyl,
$R^4$ is $CH_3$ and
$R^5$ is $CH_2$—$CH(CH_3)_2$ and $CH(CH_3)_2$.

Particularly suitable physiologically tolerated acids are: hydrochloric acid, citric acid, tartaric acid, lactic acid, phosphoric acid, methanesulfonic acid, acetic acid, formic acid, maleic acid, fumaric acid, malic acid, succinic acid, malonic acid, sulfuric acid, L-glutamic acid, L-aspartic acid, pyruvic acid, mucic acid, benzoic acid, glucuronic acid, oxalic acid, ascorbic acid and acetylglycine.

The novel compounds can be prepared by conventional methods.

Thus, the compounds can be assembled sequentially from amino acid derivatives or by linkage of suitable small fragments. In the sequential assemblage, the peptide chain or peptolide chain is extended stepwise by one amino acid derivative each time. With fragment coupling it is possible to link together fragments of different length, it being possible in turn to obtain the fragments by sequential assemblage from amino acid derivatives or by fragment coupling. The cyclic compounds are obtained by a cyclization reaction after synthesis of the open-chain peptides or peptolides.

Both in sequential assemblage and in fragment coupling it is necessary to link the building blocks by forming an amide linkage or an ester linkage. Enzymatic and chemical methods are suitable for this.

Chemical methods for forming amide linkages are dealt with in detail by Müller, Methoden der Organischen Chemie Vol. XV/2, pp. 1–364, Thieme Verlag, Stuttgart, 1974; Stewart, Young, Solid Phase Peptide Synthesis, pp. 31–34, 71–82, Pierce Chemical Company, Rockford, 1984; Bodanszky, Klausner, Ondetti, Peptide Synthesis, pp. 85–128, John Wiley & Sons, New York, 1976, and other standard works of peptide chemistry. The azide method, the symmetric and mixed anhydride method, active esters generated in situ or preformed (e.g. cyanothiopyridylesters) and the formation of amide linkages using coupling reagents (activators), especially dicyclohexylcarbodiimide (DCC), diisopropylcarbodiimide (DIC), 1-ethoxycarbonyl-2-ethoxy-1,2-dihydroquinoline (EEDQ), 1-ethyl-3-(3-dimethylaminopropyl)carbodiimide hydrochloride (EDCI), n-propanephosphonic anhydride (PPA), bis(2-oxo-3-oxazolidinyl)phosphinic chloride (BOP-Cl), diphenylphosphoryl azide (DPPA), Castro's reagent (BOP), O-benzotriazolyl-N,N,N'N'-tetramethyluronium salts (HBTU), 2,5-diphenyl-2,3-dihydro-3-oxo-4-hydroxythiophene dioxide (Steglichs Reagenz; HOTDO) and 1,1'-carbonyldiimidazole (CDI) are particularly preferred. The coupling reagents can be used alone or in combination with additives such as 4-dimethylaminopyridine (DMAP), N-hydroxybenzotriazole (HOBt), N-hydroxybenzotriazine (HOOBt), N-hydroxysuccinimide (HOSu) or 2-hydroxypyridine.

Chemical methods for the formation of ester linkages are dealt with in detail by Müller, Methoden der Organischen Chemie Vol. E5, pp. 656–773, Thieme Verlag Stuttgart, 1985. The reaction of carboxylic acid and alcohol with dicyclohexylcarbodiimide (DCC) and 4-dimethylaminopyridine (DMAP) is particularly preferred.

Whereas it is normally possible to dispense with protective groups in enzymatic peptide synthesis, reversible protection of the reactive functional groups not involved in the formation of the amide or ester linkage on both reactants is necessary for chemical synthesis. Three protective group techniques known for amines from the literature are preferred for the chemical peptide syntheses: the benzyloxycarbonyl (Z), the t-butyloxycarbonyl (BOC) and the 9-fluorenylmethyloxycarbonyl (Fmoc) protective group techniques. Particularly suitable protective groups for OH groups are t-butyl, benzyl, 2-chloroacetyl and t-butyldimethylsilyl.

The side-chain protective groups on the trifunctional amino acid derivatives or peptide or peptolide building blocks are chosen so that they are not necessarily eliminated together. A detailed review of amino acid protective groups is given by Müller, Methoden der Organischen Chemie, Vol. XV/1, pp. 20–906, Thieme Verlag, Stuttgart, 1974.

The novel compounds have very good antiviral and antineoplastic effects and can therefore be used to treat neoplastic disorders and autoimmune diseases as well as for the control and prophylaxis of infections and transplant rejections.

The effect of the novel compounds is very selective.

The compounds according to the invention can be administered orally or parenterally (subcutaneously, intravenously, intramuscularly, intraperitoneally) in a conventional way.

The dosage depends on the age, condition and weight of the patient and on the mode of administration. The daily dose of active substance is normally about 10–1000 mg/kg of body weight on oral administration and about 0.1–35 mg/m$^2$ of body surface area on parenteral administration.

The novel compounds can be used in the conventional solid or liquid pharmaceutical forms, eg. as uncoated or (film-)coated tablets, capsules, powders, granules, suppositories or solutions. These are prepared in a conventional way. The active substances can for this purpose be processed with the conventional pharmaceutical aids such as tablet binders, fillers, preservatives, tablet disintegrants, flow regulators, plasticizers, wetting agents, dispersants, emulsifiers, solvents, retardants, antioxidants and/or propellant gases (cf. H. Sucker et al.: Pharmazeutische Technologie, Thieme Verlag, Stuttgart, 1978). The administration forms obtained in this way normally contain from 1 to 90% by weight of the active substance.

The following examples illustrate the invention:

EXAMPLE 1

Preparation of the compound I ($R^1$=benzyloxycarbonyl, $R^2$=$C_2H_5$, $R^3$=$CH_3$, $R^4$=$CH_3$, $R^5$= $CH_2$—$CH(CH_3)_2$, $X^2$=O, S configuration)

L-2-Monochloroacetoxyisovaleryl chloride (1)

11.8 g (0.1 mol) of L-2-hydroxyisovaleric acid in 50 ml of CHlCl2 were cooled to 0° C., then 11.3 g (0.1 mol) of chloroacetyl chloride in 50 ml of $CH_2Cl_2$ and then 8 ml (7.9 g, 0.1 mol) of pyridine were added. The mixture was left to stand at RT for at least 20 h. After dilution with EA, it was washed with 1N KHSO$_4$ and water, dried (MgSO$_4$) and concentrated under reduced pressure. 19.8 g (0.1 mol) of yellowish oil were obtained and were sufficiently pure for further reactions.

The chloroacetyl-protected 2-hydroxyisovaleric acid (1 eq) obtained in this way was mixed with 2 eq of thionyl chloride and heated at 50° C. for 3 h until gas evolution ceased. Excess reagent was removed under reduced pressure. The acid chloride (1) was distilled. Yield 79%, boiling point 103° C./10 Torr, $[\alpha]_D^{20}$=9.4° (c=2.7, $CH_2Cl_2$).

(2RS,4S)-2-Monochloroacetoxyisovalerylpropionic acid (2)

56 mmol (11.9 g) of (1) were disslved in 80 ml of PE and added dropwise to a methylmalonate enolate solution at −60° C., which was prepared from 49.3 ml of bis(trimethylsilyl) methylmalonate in 220 ml of THF and 120 ml of 1.6N BuLi (with the indicator benzylidenebenzylamine) at −60° C. beforehand. The mixture was allowed to reach RT overnight, was hydrolyzed with 100 ml of 2N KHSO$_4$ until the mixture was acidic, and was extracted 4 times with ether, and all the organic phases were dried (MgSO$_4$) and concentrated under reduced pressure. The remaining syrup was taken up in 100 ml of toluene, stirred for 2 h and filtered to remove insoluble methylmalonic acid, which was washed with 50 ml of toluene. The toluene extract was thoroughly extracted with saturated NaHCO$_3$ solution 3 times (100, 50, 50 ml); the combined aqueous phases were washed once with 50 ml of toluene, 80 ml of CHCl$_3$ were added, and the mixture was cautiously (foaming) acidified with solid KHSO$_4$. The aqueous phase was extracted twice more with 80 ml of CHCl$_3$ each time, and the organic phase was dried (MgSO$_4$) and concentrated under reduced pressure to yield an odorless colorless oil. Yield: 11.2 g (44.8 mmol, 80%).

The β-keto acid is about 85–90% pure and was immediately processed further. Even in the cold, storage is not possible indefinitely.

$^1$H NMR (80 MHz, CDCl$_3$): δ=9.3 (s, 1H), 5.35 (d, J=4 Hz, 0.6H), 5.25 (d, J=4 Hz, 0.4H), 4.2 (s, 2H), 3.5–4.0 (m, 1H), 2.0–2.5 (m, 1H), 1.4 (d, J=6 Hz, 3H), 1.35 (d, J=7 Hz, 3H), 1.0 (m, 6H).

(2RS,4S)-2-Monochloroacetoxyisovalerylpropionyl-L-leucine trichloroethyl ester (3)

12.8 g (51.1 mmol) of (2) and 12.7 g (51.1 mmol) of L-leucine trichloroethyl ester were dissolved in 100 ml of CH$_2$Cl$_2$, cooled to 0° C., and 10.5 g (51.1 mmol) of solid DCC were added. After 2 h at 0° C. the urea was filtered off, the filtrate was evaporated, and the residue was chromatographed with PE/EA 7/3. 14.0 g (28.3 mmol, 56%) of pure product, which solidified after 2 days, were obtained. It was possible to recrystallize a sample from diethyl ether/PE very slowly. Melting point 71°–95° C. (mixture of diastereomers).

(2RS,4S)-Hydroxyisovalerylpropionyl-L-leucine trichloroethyl ester (4)

7.00 g (14.1 mmol) of (3) were dissolved in 70 ml of dioxane and, successively, 2.14 ml (15 mmol) of triethylamine and 2.22 g (15 mmol) of pentamethylenethiourea were added, and the mixture was heated at 70° C. for 3 h. It was then concentrated under reduced pressure, taken up in EA and worked up as usual. The remaining pale yellow oil was filtered through a short silica gel column with PE/EA 7/3, and the resulting mass of crystals was dissolved in 65 ml of ether, 190 ml of PE were added, and the mixture was left to stand in an open flask. Very slow fractional crystallization resulted in colorless needles of melting point 101°–103° C. Yield: 4.6 g (11 mmol, 78%).

BOC-(3S,4R,5S)-Isostatine (TBDMS)-OH (5)

a) 7.0 g (25.3 mmol) of BOC-(3S,4R,5S)-isostatine-OH (Synthesis (1989), No. 11, 832–835) were dissolved in 80 ml of DMF. The solution was cooled and 11.1 g (163 mmol) of imidazole and 10.6 g (70.3 mmol) of TBDMS-Cl were added. The reaction mixture was left at RT for 30 min. After addition of 1.2 l of EA, the reaction mixture was quickly washed with 1N KHSO4 (200 ml) and four times with water (4×150 ml), dried over MgSO$_4$ and evaporated to dryness. Yield: 12.2 g (25.3 mmol) of oil $[\alpha]_D^{20}$=+7.7° (c=3.7, CHCl$_3$)

b) The bissilylated product (12.2 g, 25.3 mmol) was dissolved in 200 ml of dioxane, and 1N NaOH (26 ml) was added dropwise until the pH of the solution remained alkaline. Dioxane was evaporated off, 200 ml of EA were added to the residue, and 30 ml of 1N HCl were added to the vigorously stirred mixture at 0° C. The aqueous phase was extracted with EA (2×100 ml), and the combined organic phases were dried over MgSO$_4$ and evaporated to dryness. Yield: 9.9 g (25.3 mmol) of oil $[\alpha]_D^{20}$=+7.7° (c=2.64, CHCl$_3$)

N-tert-Butyloxycarbonyl-O-tert-butyldimethylsilyl(3S,4R, 5S) -isostatyl-(2RS,4S)-hydroxyisovalerylpropionyl-L-leucine trichloroethyl ester (6)

580 mg (1.49 mmol) of (5), 630 mg (1.50 mmol) of (4) and 20 mg of DMAP were dissolved in 3 ml of $CH_2Cl_2$ and, at $-30°$ C. 310 mg (1.49 mmol) of DCC in 2 ml of $CH_2Cl_2$ were added. The mixture was allowed to warm slowly to RT overnight and was diluted with diethyl ether and filtered to remove urea. The organic solution was washed quickly as usual and the remaining oil was filtered through a short silica gel column with PE/EA 8/2. Yield: 1.11 g (1.40 mmol, 94%) of colorless oil, $R_f$ (PE/EA 8/2)=0.6 (two spots). $C_{35}H_{63}N_2O_9Cl_3Si$ (790.33) Calc. C 53.19 H 8.03 N 3.54 Cl 13.46 Found C 53.31 H 8.11 N 3.54 Cl 13.23

(3S,4R,5S)-Isostatyl-(2RS,4S)-hydroxyisovalerylpropionyl-L-leucine trichloroethyl ester hydrochloride (7)

2.0 g (2.53 mmol) of (6) were dissolved in 10 ml of acetonitrile, and 2 ml of aqueous hydrofluoric acid (about 50% strength) were added. The mixture was stirred at RT for 4 h, neutralized with solid potassium bicarbonate and extracted 3 times with chloroform, and the organic extracts were dried ($MgSO_4$) and rapidly concentrated under reduced pressure. The residue was immediately taken up in 20 ml of HCl/ dioxane at 0° C. and stirred at RT for 1 h. The mixture was concentrated, evaporated 3 times with methylene chloride and dried under high vacuum. Yield: 1.55 g (2.53 mmol, quantitative).

N-Benzyloxycarbonyl-L-threonine phenacyl ester (8)

25.3 g (0.1 mol) of Z-L-threonine were suspended in 200 ml of EA, and 14 ml (0.1 mol) of triethylamine were added. While stirring, 19.0 g (0.1 mol) of solid ω-bromoacetophenone were added in one portion to result initially in a clear solution, which soon became cloudy. The mixture was left to stand for 2 d, diluted with 500 ml of EA and worked up as usual. The crystalline residue was dissolved in 420 ml of hot isopropanol, 300 ml of hot water were added, and the mixture was left to stand in the dark for 2 d. The long white needles which separated out were filtered off, washed and dried in air in the dark. Yield: 27.8 g (0.075 mol, 75%), melting point 129°–130° C., $[\alpha]_D^{25}$=32.2° (c=2.04, EA)

N-BOC-N,O-Dimethyl-L-tyrosine (9)

6.0 g of NaH suspension were washed by decantation 3 times with PE, 50 ml of THF were poured on, and the mixture was cooled to 0° C. Then 32 mmol of BOC-L-tyrosine dissolved in 110 ml of THF were slowly added dropwise, and subsequently 16 ml of methyl iodide were added. The suspension was stirred at RT with exclusion of light for 25 h, 50 ml of EA were added, and the mixture was cautiously hydrolyzed with water. It was concentrated under reduced pressure to a small volume, EA was added, and the mixture was acidified with 2N $KHSO_4$. After extraction with EA, the organic phases were washed with 10% strength sodium thiosulfate solution, dried ($MgSO_4$) and evaporated under reduced pressure. Yield: 95%.

$^1$H NMR (80 MHz, $CDCl_3$): δ=8.5 (s, 1H), 7.2 (d, 2H), 6.9 (d, 2H), 4.7 (m, 1H), 3.8 (s, 3H), 3.2 (m, 2H), 2.75 (s, 3H), 1.4 (s, 9H)

O-(tert-Butyloxycarbonyl-N,O-dimethyl-L-tyrosyl)-N-benzyloxycarbonyl-L-threonine phenacyl ester (10)

2.00 g (5.38 mmol) of (8), 1.67 g (5.4 mmol) of (9) and 70 mg (0.54 mmol) of DMAP were dissolved in 20 ml of $CH_2Cl_2$ and cooled to $-30°$ C., and 1.13 g (5.5 mmol) of DCC were added. The mixture was allowed to reach RT overnight, the urea was filered off, the filtrate was concentrated, the residue was taken up in ether and left to stand for 1 h, and the urea was again filtered off. Sufficiently pure peptolide (10) was obtained by filtration through silica gel with PE/EA 7/3. Yield: 3.5 g (5.28 mmol, 98%), $[\alpha]_D^{20}$=28.7° (c=0.96, $CHCl_3$)

O-(N,O-Dimethyl-L-tyrosyl)-N-benzyloxycarbonyl-L-threonine phenacyl ester (11)

3.5 g (5.28 mmol) of (10) were dissolved in 20 ml of 5N HCl/ dioxane at 0° C. and, after 10 min, left to stand at RT for a further 2 h. The dioxane was removed under reduced pressure, the residue was dissolved in a little EA, the solution was slowly added dropwise to 200 ml of vigorously stirred diethyl ether and the mixture was stirred for a further 2 h. The precipitate was filtered off with suction and dried under reduced pressure.

Yield: 2.80 g (4.67 mmol, 88%). $C_{31}H_{35}N_2O_8Cl$ (599.08) Calc. C 62.15 H 5.89 N 4.67 Found C 61.56 H 5.99 N 4.59

The resulting product was dissolved in 30 ml of chloroform and shaken with 20 ml of 1N $KHCO_3$. The aqueous phase was extracted twice more with chloroform, and the combiised organic phases were dried ($MgSO_4$) and evaporated under reduced pressure.

Yield: 2.45 g (4.35 mmol, 93%) of colorless foam, $R_f$ (PE/EA 1/1)=0.2.

O-(tert-Butyloxycarbonyl-L-prolyl-N, O-dimethyl-L-tyrosyl)-N-benzyloxycarbonyl-L-threonine phenacyl ester (12)

2.35 g (4.18 mmol) of (11) and 0.94 g (4.38 mmol) of BOC-L-proline were dissolved in 6 ml of methylene chloride and, at $-20°$ C., 1.19 g (1.6 ml, 9.2 mmol) of ethyldiisopropylamine and 1.17 g (4.6 mmol) of BOP-Cl were added, and the mixture was slowly warmed to RT overnight. After dilution with methylene chloride, the mixture was worked up as usual and filtered through a short silica gel column with PE/EA 4/6.

Yield: 3.02 g (3.97 mmol, 95%), Rs (PE/EA 1/1)=0.4 $C_{41}H_{47}N_3O_{11}$ (757.85) Calc. C 64.81 H 6.50 N 5.53 Found C 64.71 H 6.53 N 5.46

O-(tert-Butyloxycarbonyl-L-prolyl-N, O-dimethyl-L-tyrosyl)-N-benzyloxycarbonyl-L-threonine (13)

2.80 g (3.68 mmol) of (12) were stirred with 1.8 g of zinc powder in 20 ml of 90% strength aqueous acetic acid at RT for 4 h; undissolved zinc was filtered off, and the filtrate was concentrated under reduced pressure. The residue was partitioned between EA and 1N $KHSO_4$. The combined organic phases were dried ($MgSO_4$) and concentrated under reduced pressure. The remaining resin was evaporated with toluene 3 times under reduced pressure. It was then taken up in 10 ml of 1N $KHCO_3$, the solution was extracted twice with ether, and the ether phases were back-extracted twice with $H_2O$. EA was added to the combined aqueous phases, which were acidified with 1N $KHSO_4$ while cooling. The mixture was extracted twice more with EA, and the combined organic solutions were dried ($MgSO_4$) and evaporated under reduced pressure. Yield: 2.25 g (3.5 mmol, 95%).

O-(tert-Butyloxycarbonyl-L-prolyl-N,O-dimethyl-L-tyrosyl)-N-benzyloxycarbonyl-L-threonyl-(3S,4R,5S)-isostatyl -(2RS,4S)-hydroxyisovalerylpropionyl-L-leucinetrichloroethyl ester (14)

1.55 g (2.53 mmol) of (7) and 1.79 g (2.78 mmol) of (13) were dissolved in 10 ml of $CH_2Cl_2$, cooled to 0° C., 708 mg (2.78 mmol) of BOP-Cl and 1.15 g (1.55 ml, 8.9 mmol) of ethyldiisopropylamine were added, and the mixture was slowly warmed to RT overnight. It was diluted with methylene chloride and then worked up as usual. Filtration through silica gel with PE/EA 1/1 resulted in 2.43 g (2.02 mmol, 80%) of hexapeptolide (14).

MS (FD, 50° C.): 1198 (M+1) $C_{57}H_{82}N_5O_{16}$ (1199.66) Calc. C 57.06 H 6.89 N 5.84 C18.86 Found C 57.30 H 6.82 N 5.65 C18.72

O-(tert-Butyloxycarbonyl-L-prolyl-N,O-dimethyl-L-tyrosyl)-N-benzyloxycarbonyl-L-threonyl(3S,4R,5S) -isostatyl-(2RS,4S)-hydroxyisovalerylpropionyl-L-leucine (15)

690 mg (0.57 mmol) of trichloroethyl ester (14) were dissolved in 20 ml of 90% strength aqueous acetic acid and stirred with 2 g of zinc powder overnight. The mixture was filtered, and the filtrate was concentrated under reduced pressure. The residue was taken up in EA and washed with 1N $KHSO_4$ and water. The organic phases were dried ($MgSO_4$) and evaporated under reduced pressure. The residue was evaporated with toluene 3 times under reduced pressure. Yield: 610 mg (0.57 mmol) of resin. Cyclo-[N-benzyloxycarbonyl-O-[[N-[(2S,3S,4S)-4-[(3S,4R,5S)-4-amino-3-(hydroxy) -5-methylheptanoyl]oxy-3-(hydroxy)-2,5-dimethylhexanoyl]-L-leucyl]-L-prolyl-N, O-dimethyl-L-tyrosyl]-L-threonyl] (17)

a) Preparation of the pentafluorophenyl ester (16)

22.6 mg (0.11 mmol) of DCC in 0.1 ml of $CH_2Cl_2$ were added to 106 mg (0.1 mmol) of hexapeptolide acid (15) and 22.1 mg (0.12 mmol) of pentafluorophenol in 0.5 ml of $CH_2Cl_2$ at −20° C. The mixture was allowed to reach RT overnight. This solution was used without further treatment for the elimination of the BOC protective group.

b) Ring closure 0.1 mmol of pentafluorophenyl ester (16) were diluted to 1 ml with methylene chloride. Then, at 0° C., 0.5 ml of trifluoroacetic acid was injected, and the mixture was kept at 0° C. for 3 h. Solvent and excess acid were stripped off under reduced pressure, and the residue was dissolved in 200 ml of chloroform.

This solution was vigorously shaken with 50 ml of saturated sodium bicarbonate solution in a separating funnel for 5 min. The mixture was then left to stand for 1 h, the chloroform layer was separated off, and the aqueous phase was washed 3 times more with 30 ml of chloroform each time. The organic solutions were dried ($MgSO_4$) and concentrated under reduced pressure. Chromatography with PE/EA 35/65 separated the epimeric rings.

Yield: 48 mg (0.051 mmol, 51%) of (2S)-Hip epimer; 23 mg (0.024 mmol, 24%) of (2R)-Hip epimer. (2S)-Hip epimer $[\alpha]_D^{25} = -147.5°$ (c=0.72, EA) MS: 950 (M+1, 24%) $C_{50}H_{71}N_5O_{13}$ (950.14) Calc. C 63.21 H 7.53 N 7.37 Found C 63.13 H 7.55 N 7.32

EXAMPLE 2

Cyclo-[N-hexanoyl-O-[[N-[(2S,3S,4S)-4-[(3S,4R,5S)-4-amino-3 -(hydroxy)-5-methylheptanoyl]oxy-3-(hydroxy)-2,5-dimethyl-hexanoyl]-L-leucyl]-L-prolyl-N, O-dimethyl-L-tyrosyl]-L-threonyl] (18)

550 mg (0,158 mmol) of (17) were dissolved in 40 ml of 90% strength aqueous acetic acid, 1.1 ml of 1N HCl were added, and the mixture was hydrogenated with 150 mg of Pd/C under atmospheric pressure for 6 h. It was then worked up as usual, and the residue was evaporated with 5 ml of toluene twice under reduced pressure. The hydrochloride was left as a white powder. The hydrogenation resulted in each case in the more stable (2S)-Hip epimer.

0.09 ml of hexanoyl chloride (0.65 mmol) and 0.33 ml of collidine (2.5 mmol) were added to a solution of 500 mg of the resulting hydrochloride (0.58 mmol) in 10 ml of absolute $CH_2Cl_2$ at −10° C. The mixture was stirred at −10° C. for 2 h and at RT for 1 h. The $CH_2Cl_2$ was stripped off under reduced pressure, the residue was dissolved in EA, and the solution was washed with 1N $H_2SO_4$ and N $KHCO_3$ solution. The organic phase was dried with $MgSO_4$ and concentrated. Recrystallization of the residue from EA/PE 1:1 yielded 400 mg of pure (18). The filtrate was concentrated and purified by MPLC (EA/PE 7/3). Overall yield: 480 mg=90%.

The following compounds I can be prepared as in Examples 1 and 2:

| No. | $R^1$ |
|---|---|
| A: $X^1 = O$, $X^2 = O$, $R^2 = C_2H_5$, $R^3 = CH_3$, $R^4 = CH_3$, $R^5 = CH_2—CH(CH_3)_2$ S configuration | |
| 3 | $CH_3—CO$ |
| 4 | $H—CO$ |
| 5 | $CH_3—CH_2—CO$ |
| 6 | $CH_3—(CH_2)_{14}—CO$ |
| 7 | Z |
| 8 | BOC |
| 9 | $CH_3—CH_2—O—CO$ |
| 10 | Z—N—Me—D-Ala— |
| 11 | p-OH-benzoyl |
| 12 | $(CH_3)_3C—CO$ |
| 13 | $HO—(CH_2)_3—CO$ |
| 14 | $C_6H_5—O—CO$ |
| 15 | $CF_3—CO$ |
| 16 | $(CF_3)_2CH—O—CO$ |
| 17 | $CH_3—CH_2—O—CO—(CF_2)_2—CO$ |
| 18 | p-$HO—C_6H_4—(CH_2)_2—CO$ |
| 19 | $CH_3—CO—CH_2—CO$ |
| 20 | $CF_3—CH_2—O—CO$ |
| 21 | Ac-sarcosyl |
| B: $X^1 = O$, $X^2 = O$, $R^2 = C_2H_5$, $R^3 = CH_3$, $R^4 = CH_3$, $R^5 = CH_2—CH(CH_2)_2$ R configuration | |
| 22 | n-hexanoyl |
| 23 | Ac—N—Me—D-Leu |
| C: $X^1 = O$, $X^2 = O$, $R^2 = CH_3$, $R^3 = CH_3$, $R^4 = CH_3$, $R^5 = CH_2—CH(CH_3)_2$ S configuration | |
| 24 | $CH_3—CO$ |
| 25 | $CH_3(CH_2)_4CO$ |
| 26 | naphthyl-1-sulfonyl |
| 27 | $H—CO$ |
| 28 | $CH_3—CH_2—CO$ |
| 29 | $CH_3—C(CH_2)_{14}—CO$ |
| 30 | Z |
| 31 | BOC |
| 32 | $CH_3—CH_2—O—CO$ |
| 33 | Z—N—Me—D-Ala |
| 34 | Ac-sarcosyl |
| 35 | p-HO-benzoyl |
| 36 | $(CH_3)_3C—CO$ |
| 37 | $HO—(CH_2)_3—CO$ |
| 38 | $C_6H_5—O—CO$ |
| 39 | $CF_3—CO$ |
| 40 | $(CF_3)_2CH—O—CO$ |
| 41 | $CH_3—CH_2—O—CO—(CF_2)_2—CO$ |
| 42 | p-$HO—C_6H_4—(CH_2)_2—CO$ |
| 43 | $CH_3—CO—CH_2—CO$ |
| 44 | $CF_3—CH_2—O—CO$ |
| D: $X^1 = O$, $X^2 = O$, $R^2 = CH_3$, $R^3 = CH_3$, $R^4 = CH_3$, $R^5 = CH_2—CH(CH_3)_2$ R configuration | |
| 45 | $CH_3—CO$ |
| 46 | $CH_3—C(CH_2)_4—CO$ |
| 47 | $(CH_3)_2CH—CO$ |
| 48: $X^1 = O$, $X^2 = O$, $R^1 = Z—N—Me—D-Leu$, $R^2 = C_2H_5$, $R^3 = CH_3$, $R^4 = H$, $R^5 = CH_2—CH(CH_3)_2$ S configuration | |

Example 49

Preparation of the compound I ($R^1$=benzyloxycarbonyl, $R^2=C_2H_5$, $R^3=CH_3$, $R^4=CH_3$, $R^5=CH_2—CH(CH_3)_2$, $X^1$=NH, $X^2$=O, S configuration)

Methyl N'-benzyloxycarbonyl-$N^\beta$-[tert-butyloxycarbonyl-N,O-dimethyl-L-tyrosyl] -(2S,3R)-diaminobutyrate (19)

6 mmol (1.82 g) of Z—Dab—OMe. HCl (Hoppe-Seyler's Z. Physiol. Chem. 354, (1973) 689) were partitioned between EA and NaHCO$_3$ solution, and the aqueous phase was extracted twice more with EA. The combined organic phases were dried with magnesium sulfate and evaporated, and the residue was dissolved with 6.3 mmol (1.95 g) of BOC-N,O-dimethyl-L-tyrosine in 15 ml of dichloromethane and, at −20° C., 6.3 mmol (1.30 g) of DCC were added.

After the mixture had been warmed to RT overnight it was diluted with a large amount of diethyl ether, filtered and evaporated. The residue was again taken up in ether, left to stand for 1 h, filtered and evaporated. Filtration through silica gel and medium pressure chromatography (PE/EA=1/1) yielded 3.04 g (91%) of colorless foam.

Melting point: 46°–48° C.; $[\alpha]_D^{20}$=2.3° (c=1.1; CHCl$_3$); TLC (PE/EA=1/1): R$_f$=0.33; HPLC (Hex/EA=1/1): t$_R$=3.6 min;

Methyl N$^\epsilon$-benzyloxycarbonyl-N$^\beta$-[tert-buttyloxycarbonyl-L-prolyl-N,O-dimethyl-L-tyrosyl] -(2S,3R)-diaminobutyrate (20)

4.8 mmol (2.68 g) of (19) were dissolved in 5 ml of dichloromethane, 10 ml of HCl/dioxane were added, and the mixture was stirred at RT for 1 h. It was then evaporated, the residue was taken up in EA, and the solution was vigorously shaken with NaHCO$_3$ solution. The aqueous phase was extracted twice more with EA. The combined organic phases were dried with magnesium sulfate, filtered and evaporated.

The resulting colorless foam was dissolved with 5 mmol (1.08 g) of BOC-L-proline in 15 ml of dichloromethane and, at −20° C. first 5 mmol (1.27 g) of BOP-Cl and then 11 mmol (1.42 g) of ethyldiisopropylamine were added.

The mixture was allowed to warm to RT overnight, worked up as usual and filtered through silica gel. Medium pressure chromatography (PE/EA=4/6) resulted in 2.77 g (88%) of colorless foam. $[\alpha]_D^{20}$=−55.1° (c=1.0; CHCl$_3$); TLC (PE/EA=4.6): R$_f$= 0.3; HPLC (Hex/EA=4/6): t$_R$=4.8 min;

N$^\epsilon$-Benzyloxycarbonyl-N$^\beta$-[tert-butyloxycarbonyl-L-prolyl-N,O-dimethyl-L-tyrosyl] -(2S,3R)-diaminobutyric acid (21)

4 ml of 1N NaOH were slowly added dropwise, monitoring the pH (pH <10), to 3.5 mmol (2.29 g) of (20) in 15 ml of dioxane/water (2:1). After conversion was substantially complete (checked by TLC), the dioxane was removed under reduced pressure, and the aqueous phase was extracted twice with diethyl ether. It was possible where appropriate to recover unreacted ester from the ether phase, while EA was added to the aqueous phase which was then acidified to pH 1–2 at 0° C. with solid potassium bisulfate. Repeated extraction with EA, drying of the organic phases with magnesium sulfate and evaporation of the solvent resulted in the corresponding carboxylic acid. Yield: 2.1 g (93.7%) of colorless, amorphous solid;

N$^\epsilon$-Benzyloxycarbonyl-N$^\beta$-[tert-butyloxycarbonyl-L-prolyl-N,O-dimethyl-L-tyrosyl] -(2S,3R)-diaminobutyryl(2S,4R,5S)-isostatyl-(2RS,4S)-oxyisovalerylpropionyl-L-leucine trichloroethyl ester (22)

1.1 mmol (705 mg) of (21) and 1.1 mmol (674 mg) of (7) were dissolved in 8 ml of dichloromethane and, at 0° C. 11 mmol (280 mg) of BOP-Cl and 3.4 mmol (440 mg) of ethyldiisopropylamine were added and the mixture was warmed to RT overnight. The usual working up and medium pressure chromatography (PE/EA=3/7) resulted in 570 mg (43%) of colorless foam. TLC (PE/EA=3/7): R$_f$=0.32; HPLC (Hex/EA=3/7): t$_R$=3.1 min;

N$^{68}$ -Benzyloxycarbonyl-N$^\beta$-[tert-butyloxycarbonyl-L-prolyl-N,O-dimethyl-L-tyrosyl] -(2S, 3R)-diaminobutyryl(2S, 4R, 5S)-isostatyl-(2RS, 4S)-oxyisovalerylpropionyl-L-leucine (23)

0.475 mmol of trichloroethyl ester (22) were dissolved in 20 ml of 90% strength aqueous acetic acid and stirred vigorously with 2 g of zinc powder (freshly etched with hydrochloric acid and washed with water, ethanol and ether) overnight.

After filtration, the acetic acid was stripped off under oil pump vacuum, the residue was taken up in EA, and the solution was washed with 10% strength citric acid, dried with magnesium sulfate, filtered and concentrated. For complete removal of the acetic acid, the residue was evaporated twice more with toluene and dried under high vacuum. Yield: 453 mg (89.3%) of colorless solid;

Cyclo-[N$^\epsilon$-benzyloxycarbonyl-N$^\beta$-[[N-[(2S,3S,4S)-4-[(3S,4R,5S)-4-amino-3-(hydroxy)-5-methylheptanoyl]oxy-3-(hydroxy)-2,5-dimethylhexanoyl] -L-leucyl]-L-prolyl-N,O-dimethyl-L-tyrosyl]-(2S, 3R)-diaminobutyryl] (24 )

0.374 mmol (400 mg) of hexapeptolide acid are reacted by the general method for the ring closure.

a) Preparation of the pentafluorophenyl ester and elimination of the BOC protective group 0.45 mmol of DCC were added to 400 mg of (23) (0.374 mmol) and 0.56 mmol of pentafluorophenol in 2 ml of dichloromethane at −20° C., and the mixture was warmed to RT overnight. It was filtered and concentrated and, at 0° C., 1 ml of trifluoroacetic acid was immediately added and stirred for 1–4 h. The trifluoroacetic acid was then removed under high vacuum, and the resulting resin was used for the ring closure. Both reaction steps were checked by TLC for completeness.

b) Ring closure

The resin (0.37 mmol) obtained from the BOC elimination was taken up in 400 ml of dry chloroform and shaken vigorously with 100 ml of saturated sodium bicarbonate solution for 5 min. The mixture was left to stand for 1 h, and then the aqueous phase was extracted twice more with chloroform. The combined organic phases were dried with magnesium sulfate, filtered and evaporated.

Dicyclohexylurea was removed by taking up the residue in absolute diethyl ether, leaving to stand for 1 h and filtering through a Pasteur pipette packed with cotton.

Pentafluorophenol was removed by filtration through silica gel with dichloromethane. The product remained on the silica gel and was subsequently eluted with EA. Final purification then took place by medium pressure chromatography.

Medium pressure chromatography (PE/EA=35/65) yielded 150 mg (42.2%) of colorless solid. TLC (PE/EA= 35/65): R$_f$=0.34; melting point: 112° C.; $[\alpha]_D^{20}$32 −165.3° (c=0.9; CHCl$_3$); MS: 948.4 (M), 949.4 (M+H);

Cyclo-[Nε-[Z-N-Me-D-leucyl]-N$^\beta$-[[N-[(2S,3S,4S)-4-[(3S,4R,5S) -4-amino-3-(hydroxy)-5-methylheptanoyl]oxy-3-(hydroxy)-2,5-dimethylhexanoyl] -L-leucyl]-L-prolyl-N, O-dimethyl-L-tyrosyl]-(2S,3R)-diaminobutyryl] (25)

0.084 mmol of (24) in 10 ml of 90% strength aqueous acetic acid with 200 μl of 1N HCl and 30 mg of Pd/C was hydrogenated at RT under 1 bar for 6 h (TLC check).

The catalyst was filtered off, the acetic acid was stripped off under reduced pressure, and the residue was evaporated twice with toluene to provide the cyclopeptolide hydrochloride in quantitative yield.

0.12 mmol of Z-N-Me-D-Leu 3-cyano-4,6-dimethyl-2-thiopyridyl ester and 0.12 mmol of triethylamine were added to the cyclopeptolide hydrochloride in 0.5 ml of dichloromethane at 0° C. The mixture was then stirred at RT overnight and worked up as follows.

First the yellow thiopyridone derivative was filtered off, and the filtrate was concentrated and loaded onto a short silica gel column. Excess thiopyridyl ester was removed by washing with PE/EA=7/3. The product was then eluted with PE/EA=2/8. The crude product free of thiopyridyl ester was then washed in EA with 10% strength citric acid, 1N NaOH (removal of the remaining thiopyridone) and saturated brine, dried with magnesium sulfate and evaporated.

Medium pressure chromatography (PE/EA=3/7) resulted in 62 mg (68.6%) of colorless solid. Melting point: 102°–103° C., TLC (PE/EA=3/7): $R_f$=0.25; $[\alpha]_D^{20}$=–113° (c=0.9; $CHCl_3$);

The following compounds of the formula I can be prepared in a similar way (in some cases using the appropriate norstatine derivative and/or the appropriate D-tyrosine derivative and/or (2RS,4S)-fluorenylmethyloxy-carbonylaminoisovaleryl-propionic acid and/or (2S)-2,3-diaminopropionic acid).

| No. | $R^1$ |
|---|---|
| F: $X^1$ = NH, $X^2$ = O, $R^2$ = $C_2H_5$, $R^3$ = $CH_3$, $R^4$ = $CH_3$, $R^5$ = $CH_2$—$CH(CH_3)_2$, S configuration | |
| 51 | BOC—N—Me—D-Leu |
| 52 | Ac-sarcosyl |
| 53 | $CH_3CO$ |
| 54 | $CH_3(CH_2)_4CO$ |
| 55 | $CF_3CO$ |
| 56 | PhOCO |
| 57 | p-OH-benzoyl |
| 58 | Z—N—Me—D-Ala |
| 59 | $CH_3CH_2OCO$— |
| 60 | Ac—Gly |
| 61 | Naphthalene-2-sulfonyl |
| 62 | N—Me—D-Val |
| 63 | Perfluoropropionyl |
| 64 | BOC |
| 65 | Ethyloxycarbonyl |
| G: $X^1$ = NH, $X^2$ = NH, $R^2$ = $CH_3$, $R^3$ = $CH_3$, $R^4$ = $CH_3$, $R^5$ = $CH_2$—$CH(CH_3)_2$, S configuration | |
| 66 | $CH_3$—CO |
| 67 | $CH_3$—$C(CH_2)_4$—CO |
| 68 | Z—N—Me—D-Leu |
| 69 | Z-sarcosyl |
| H: $X^1$ = NH, $X^2$ = NH, $R^2$ = $CH_3$, $R^3$ = H, $R^4$ = $CH_3$, $R^5$ = $CH_2$—$CH(CH_3)_2$, S configuration | |
| 70 | $CH_3CO$ |
| 71 | $CH_3(CH_2)_4CO$ |
| 72 | BOC—N—Me—D-Leu |
| 73 | $CF_3CO$ |
| 74 | p-OH-benzoyl |
| 75 | Ac-sarcosyl |
| 76 | $HC(CF_3)_2OCO$ |
| 77 | PHOCO |
| I: $X^1$ = NH, $X^2$ = O, $R^2$ = $CH_3$, $R^3$ = H, $R^4$ = $CH_3$, $R^5$ = $CH_2$—$CH(CH_3)_2$, | |
| 78 | $CH_3CO$ |
| 79 | HCO |
| 80 | $CH_3(CH_2)_4CO$ |
| 81 | $(CH_3)_3CO$ |
| 82 | $CF_3CO$ |
| 83 | p-OH-benzoyl |
| 84 | Z |
| 85 | BOC |
| 86 | Z—N—Me—D-Ala |
| 87 | Z—N—Me—D-Leu |
| 88 | Ac-sarcosyl |
| 89 | PhOCO |
| 90 | $HC(CF_3)_2OCO$ |
| 91 | $CH_3CH_2OCO$—N—Me—D-Leu |
| 92 | $CF_3CH_2OCO$ |
| 93 | Naphthalene-1-sulfonyl |
| 94 | Naphthalene-2-sulfonyl |
| 95 | Perfluoroheptanoyl |

Cytotoxicity test

The cytotoxicity was tested in a widely used standard system for adherent cell lines by the method of Flick and Gifford (crystal violet assay) [J. Immunol. Meth., 1984; 68 (1984) 167–175]. The target cells used were the human cell lines CX-I (colon carcinoma), MX-I (breast carcinoma) and LX-I (lung carcinoma).

The cells were in each case plated out at a density of 2–3×$10^3$ cells per well in flat-bottom 96-well microtiter plates and incubated under standard conditions (RPMI 1640 with 10% fetal calf serum and 1% nonessential amino acids) at 37° C. and 5% $CO_2$/95% air for 24 h. The cells were then incubated under the same conditions but in the presence of various concentrations of the test compounds (controls only in medium) for a further 72 h. The cytotoxic activity was quantified after removal of the culture medium and thus of the nonadherent, dead cells. The remaining adherent cells were incubated with 50 µl of a crystal violet solution for 20 min and subsequently the microtiter plates were thoroughly washed with water to remove unbound, watersoluble dye.

The remaining water-insoluble dye crystals in each well were dissolved in 100 µl of a solution composed of 50% EtOH and 0.1% acetic acid. The absorption of each well was determined using a microtiter plate photometer (Titertec, Multiscan, Flow Lab., Meckenheim, FRG), and the half maximum effective concentration of each test substance was calculated.

In this test the novel compounds showed a good cytotoxic effect on the tested human tumor cell lines.

The meanings of the abbreviations used in the examples are as follows:

Ac: Acetyl

Eq: Equivalent(s)

BOC: t-Butyloxycarbonyl

BOP-Cl: Bis(2-oxo-3-oxazolidinyl)phosphinic chloride

Dab: (2S,3R)-Diaminobutyric acid

TLC: Thin-layer chromatography

DCC: Dicyclohexylcarbodiimide

DMAP: 4-Dimethylaminopyridine

EA: Ethyl acetate

Hip: Hydroxyisovalerylpropionic acid

Ist: Isostatine

MCA: Monochloroacetyl

NMR: Nuclear magnetic resonance

PE: Petroleum ether

Tce: Trichloroethyl

RT: Room temperature

TBDMS: tert-Butyldimethylsilyl

THF: Tetrahydrofuran

Z: Benzyloxycarbonyl

We claim:

1. A peptide of the formula

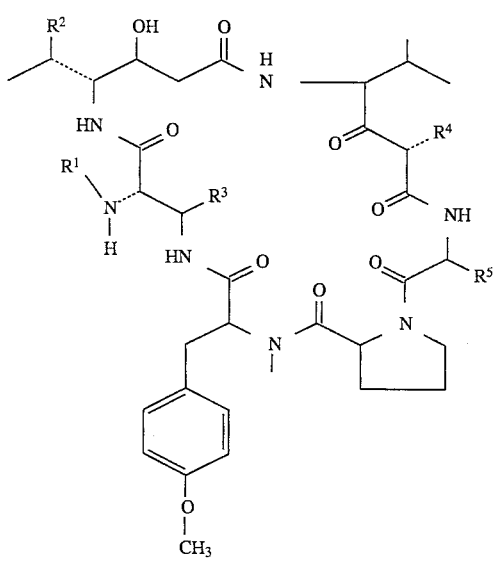

where
R¹ is an amino-protective group, a linear, branched or alicyclic saturated or unsaturated aliphatic, aliphatic-aromatic or aromatic acyl radical which has 1–30 carbons and can be substituted by fluorine, nitro, oxo, hydroxyl, $C_1$–$C_4$-alkoxy or unprotected or protected amino, $R^2$ is hydrogen, methyl or ethyl, $R^3$ is hydrogen or methyl, $R^4$ is hydrogen or methyl, and $R^5$ is hydrogen or $C_1$–$C_4$-alkyl, and the salts thereof with physiologically tolerated acids.

* * * * *